United States Patent [19]

Kampner

[11] Patent Number: 4,627,423

[45] Date of Patent: Dec. 9, 1986

[54] PORTABLE TRACTION DEVICE

[76] Inventor: Stanley L. Kampner, 1270 Armsby St., Hillsborough, Calif. 94010

[21] Appl. No.: 649,091

[22] Filed: Sep. 10, 1984

[51] Int. Cl.[4] .......................... A61H 1/02; A61F 5/00

[52] U.S. Cl. ....................................... 128/75; 128/71; 5/443

[58] Field of Search ...................... 5/312, 443; 128/69, 128/75, 71

[56] References Cited

U.S. PATENT DOCUMENTS

| | | | |
|---|---|---|---|
| 1,319,849 | 10/1919 | Colegrove | 5/312 |
| 2,796,061 | 6/1957 | Miller | 128/75 |
| 3,472,224 | 10/1969 | Ewerwahn | 5/443 |
| 3,856,003 | 12/1974 | Pfluger | 128/75 |
| 3,871,366 | 3/1975 | Cotrel | 128/75 |
| 4,508,109 | 4/1985 | Saunders | 128/69 |
| 4,524,763 | 6/1985 | Eberling | 128/75 |

FOREIGN PATENT DOCUMENTS

| | | | |
|---|---|---|---|
| 2622255 | 11/1977 | Fed. Rep. of Germany | 128/75 |

*Primary Examiner*—William Pieprz
*Assistant Examiner*—Tonya Eckstine
*Attorney, Agent, or Firm*—Townsend and Townsend

[57] ABSTRACT

A self-contained traction device for pelvic or cervical spine traction which can be placed on an ordinary bed is disclosed. A platform with an upwardly inclined surface is used for elevating a portion of a patient's body. A strap is attached to the portion of the patient's body to which traction is to be applied, and the other end of the strap is attached to a cable which passes over a pulley attached to the far end of the platform. The far end of the cable on the other side of the pulley is attached to a weight which provides the traction force. Because the weight is directly attached through the pulley to the platform against which the patient rests, the horizontal forces exerted by the patient's body upon being pulled by the strap are cancelled by the horizontal forces applied by the weight through the pulley to the platform so that movement of the traction device across the bed is prevented without the need for restraining it to a bed frame or the like.

14 Claims, 8 Drawing Figures

PORTABLE TRACTION DEVICE

BACKGROUND OF THE INVENTION

This invention relates to traction devices which can be used at home to apply pelvic traction to the lumbar region of the patient's spine or to apply cervical spine traction. Pelvic traction serves to distract, or pull apart, the intervertebral discs and apophyseal joints of the spine thus taking pressure off of any nerve roots which may be pinched while keeping the apophyseal joints and ligaments at rest. The preferred direction of such traction is towards the patient's feet at an upward incline. The optimal position for easing pressure on such pinched nerves, whether or not traction is applied, is to have the patient lie on his back with his legs elevated. By applying pelvic traction while the patient is in such optimal position, the effect of the traction is to exert a lever action on the spine, thus increasing the beneficial effects of the traction.

Numerous traction devices exist for applying traction to the lumbar region of a patient's spine which are attachable to the frame of a standard hospital bed. A hospital bed can be rented for applying traction in one's home, but this can be expensive and cumbersome and could be impractical if there is no room in the home for bringing in the large hospital bed.

Traction devices for home use must be capable of operating without the benefit of a hospital bed frame. Typically such home traction devices compromise some aspects of an ideal hospital traction. U.S. Pat. No. 4,362,151 issued to Cottrell shows a triangular support with a pulley near the top. Although the patient's body is placed in an optimal position by placing his calves over a stool, the patient must pull the traction straps with his hands and the traction applied is upward and away from the patient's feet, rather than the ideal direction. In another device shown in U.S. Pat. No. 3,398,742 issued to Alexander, a stand placed at the foot of a bed applies traction in an optimal direction, but there is no provision for placing the patient's body in the optimal position.

Other devices exist for applying cervical spine traction. Cervical spine traction is often used to treat acute or chronic neck pain where surgical intervention is not required. The aim of such traction is to distract the cervical spine discs and joints. The ideal position for the patient while traction is applied is semi-recumbent with the head slightly raised to produce a slight flexion of the cervical spine. This position allows the patient to be totally relaxed and takes the weight of the head off the cervical spine. A patient can stay in this position for an extended length of time and still comfortably read, etc.

Cervical spine traction devices designed for use in a hospital are impractical for home use because of the need for a hospital bed. Home traction devices typically compromise some aspect of the ideal hospital traction. One type of device attaches to the top of a door and applies traction to a patient seated in a chair. Not only are these devices uncomfortable, they pull in a less than ideal direction while the patient is not in an ideal position. Other home traction devices are frames which attach to the head of a bed and apply traction to a patient in a totally supine position. The totally supine position is not as ideal as a semi-recumbent position and a patient is unable to read, etc. in such a position.

The present invention provides a home traction device for pelvic traction and cervical spine traction which does not compromise any of the beneficial aspects of ideal hospital traction.

SUMMARY OF THE INVENTION

The present invention is a self-contained traction device which can be placed on an ordinary bed. A platform with an upwardly inclined surface is used for elevating a portion of a patient's body. A strap is attached to the portion of the patient's body to which traction is to be applied, and the other end of the strap is attached to a cable which passes over a pulley attached to the far end of the platform. The far end of the cable on the other side of the pulley is attached to a weight which provides the traction force.

Because the weight is directly attached through the pulley to the platform against which the patient rests, the horizontal forces exerted by the patient's body upon being pulled by the strap are equal and opposite to the horizontal forces applied by the weight through the pulley to the platform. Therefore, movement of the traction device across the bed is prevented without the need for attaching restraining cables from the platform to a bed frame as required by other devices where the pulley is attached to the frame of the bed, thus requiring a hospital bed frame to attach the pulley and restraining cables to.

In the preferred embodiment, the platform has a pair of L-shaped legs attached at one end of the platform with the other end of the legs resting on the floor to provide further stability. The legs are adjustable in both length and height. The pulley is attached to the platform by an elongated member which telescopes out away from the platform at an angle away from the patient's body. The telescoping member allows the angle of traction to be adjusted to obtain an optimum angle.

In the embodiment used for cervical spine traction, the platform is triangular in shape with a flat surface extending upward from the surface of the bed to where the telescoping member with the pulley attaches to the platform. The patient rests with his back against the slanted surface and the strap attached around his head. The slanted surface allows the patient to lie in a semi-recumbent position, which is the ideal position for cervical spine traction.

In the embodiment of the invention used for pelvic traction, the platform is trapezoidal in shape with a first upward sloping end against which a patient lying on his back places his thighs, extending upwards from his hips, a top portion against which the patient's calves rest and a second vertical end to which the telescoping member and pulley are attached. This embodiment places the patient in the optimum position, on his back with his legs raised and relaxed. The telescoping member allows the angle of traction to be adjusted to obtain the optimum effect.

The platform is preferably made of plastic and has a foam rubber mattress layer for comfort. The telescoping member and leg stands retract within the platform and the platform has handles so it can be carried around like a suitcase. Its small size and lightweight plastic construction make it easy to carry. Its simple construction makes it inexpensive. The invention is thus ideal for homes or apartments where a hospital bed would be too big and for individuals who cannot afford an expensive hospital bed.

The invention thus provides, for both pelvic traction and cervical spine traction, a simple, small, lightweight, inexpensive portable traction device which can be used on any flat surface and which does not compromise any of the advantageous aspects of hospital traction.

DETAILED DESCRIPTION OF THE PREFERRED EMBODIMENTS

Figure 1:
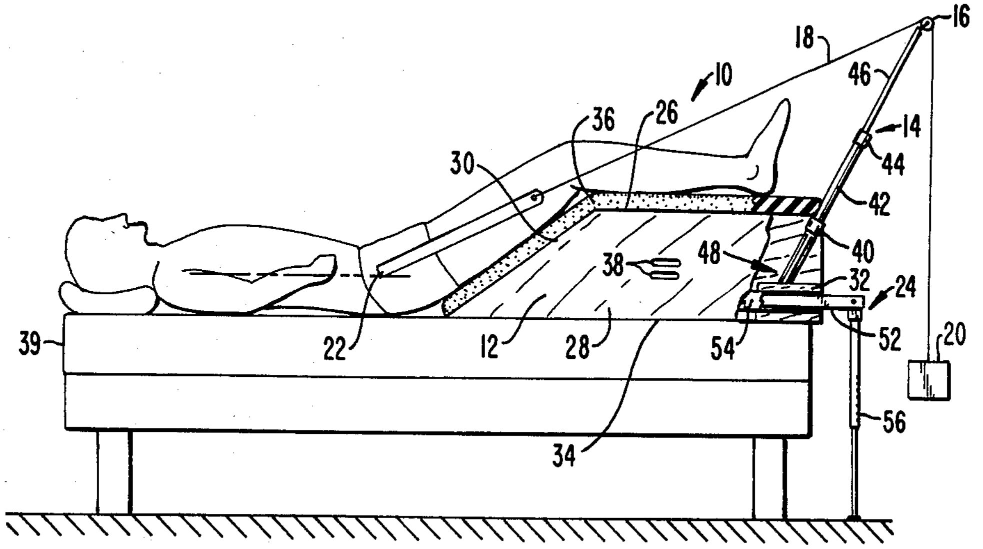
FIG. 1 is a side elevational view, partially broken away, of a first preferred embodiment of the invention for applying pelvic traction.

Referring to FIG. 1, the self-contained traction device 10 of the present invention generally comprises a platform or support structure 12 from which extends an arm 14 in an upward direction, the free end of which mounts a pulley 16. A flexible tension member, such as a strap, a cable or the like 18 is looped over the pulley. A weight 20 is attached to one end of tension member 18 while the other end is attached to a suitable harness 22. A pair of leg stands 24 are attached to the end of the platform near arm 14.

In the preferred embodiment, platform 12 is a box-like, lightweight structure made of plastic, plywood or a similar material for easy handling, carrying and storage. Platform 12 has a flat top surface 26 which is wide enough to support a patient's calves, a pair of sides 28, a sloping surface 30 to support a patient's thighs, a back vertical surface 32 and a flat bottom 34 which allows it to be placed on any flat surface. Top surface 26 and sloping surface 30 are covered with a foam layer 36 so that a patient's legs may rest thereon in comfort. A pair of slots 38 in one or more of sides 28 provide a handle so that platform 12 may be carried like a suitcase.

Arm 14 is attached to platform 12 near the upper end of back surface 32. Arm 14 telescopes so that its length may be adjusted, thus adjusting the angle at which cable 18 applies traction to the patient's body. Leg stands 24 are attached to platform 12 at the lower end of back surface 32. Leg stands 24 provide additional stability when platform 12 is placed on a raised surface, such as a bed 39. Additionally, leg stands 24 prevent a tipping of platform 12 due to the force of weight 20 after the patient has alighted therefrom.

Figure 3:
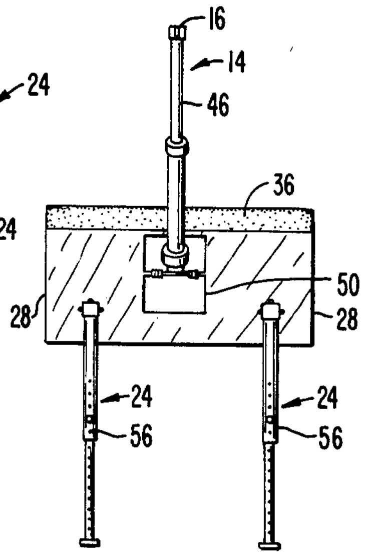
FIG. 3 is a rear elevational view of the first preferred embodiment of the invention.

Telescoping arm 14 is anchored to platform 12 by a circular tightener 40 which allows a lower member 42 of the telescoping arm to be attached to platform 12 and adjusted in length. A second tightener 44 is attached to the end of member 42 opposite platform 12 and engages a second member 46 of the telescoping arm 14 which retracts within member 42. Telescoping arm 14 retracts within a track 48 within platform 12 for storage and transportation. As can be seen in FIG. 3, a door 50 is located on the back of platform 12 to allow access to track 48 for adjusting the extension of arm 14.

Alternately, telescoping arm 14 could be detachable from platform 12 and stored inside platform 12 by the use of U-shaped clamps or the like. Telescoping arm 14 could then be attached to platform 12 by fitting it over or inside a short tube or the like extending from platform 12.

Figure 2:
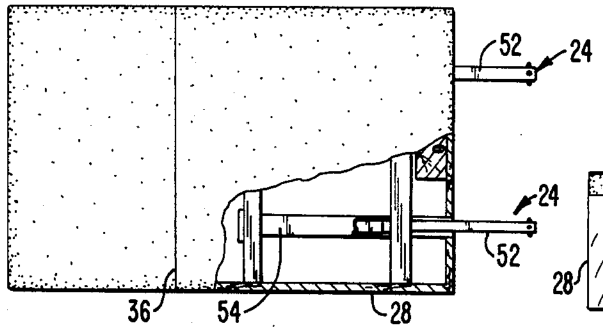
FIG. 2 is a plan view, partially broken away, of the first preferred embodiment of the invention.

A pair of L-shaped legs 24 are attached to the lower end of back surface 32 of platform 12. Each leg 24 has a horizontal arm 52 which slides in and out of a track 54 for storage and transportation, as can be seen more clearly in FIG. 2 which shows the top of platform 12. Each arm 52 is connected to a vertical leg 56 which rests on the floor.

Figure 4:
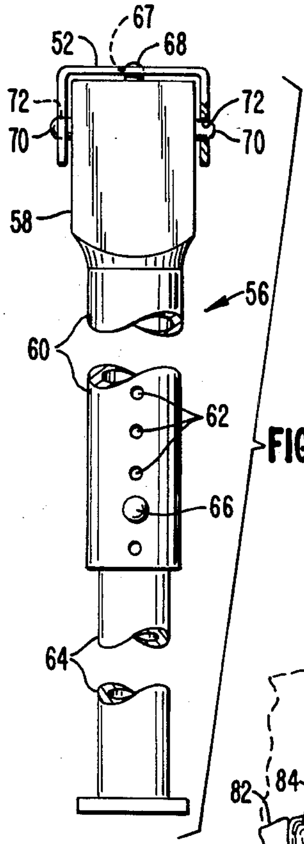
FIG. 4 is a fragmentary, rear elevational view of the preferred embodiment of a leg of the present invention.

Referring to FIG. 4, which shows the detail of leg 56, it can be seen that leg 56 has an upper portion 58 which is rectangular in shape and attaches to arm 52. Upper portion 58 is attached to a tubular member 60 of leg 56 which has a plurality of holes 62 in a evenly spaced column along its lower section. A lower portion 64 of leg 56 is another tube, narrower in diameter than tube 60, which is retractable within tube 60 and has a spring-loaded button 66 along its upper section for engaging one of holes 62.

Arm 52 has a hole 67 on its upper portion near leg 56 for receiving a fixed or spring-loaded button 68 attached to the top of leg 56. Leg 56 rotates around a pair of hinges 70 allowing it to be elevated into the same plane as arm 52. Hinges 70 are spring-loaded hinges with a pair of buttons on either end extending through a pair of holes 72 in the sides of arm 52. Arm 52 is rectangular in shape with walls on the sides and top but no wall on the bottom, allowing leg 56, when hinge 68 is disengaged and leg 56 is lifted into the same plane as arm 52, to slide within arm 52 for storage in conjunction with arm 52 by sliding back into track 54.

The height of platform 12 off of bed 39 can be varied either by providing a plurality of platforms having varying heights, or by making the platform adjustable in height, e.g., with a height adjustable bottom plate (not shown). In the preferred embodiment, platform 12 has a fixed height of approximately $11\frac{1}{2}$ inches above the bed, not including foam layer 36.

In operation, a pelvic belt which acts as a harness suitable for the intended form of traction is attached to the ends of cable 18, the patient positions himself on bed 39 so that his thighs rest on slanted surface 30, and weight 20 is applied to the free end of cable 18. The application of weight 20 generates a tension force in cable 18 between pulley 16 and harness 22 which is equal to the weight of weight 20. The horizontal force vectors applied by cable 18 to pulley 16 and to harness 22 are equal and in opposite directions. Since the patient is positioned so that his body contacts the lower portion of slanted surface 30, the horizontal force applied by cable 18 to platform 12 (or the patient) is cancelled out by the opposite horizontal force applied by the cable to pulley 16 and the platform, and relative movement of the platform over the flat surface is prevented, even though the platform is not secured thereto.

For traction devices which attach to a bed frame, the force applied to the pulley would act on the bed frame and the patient's body would have to be secured to the bed frame by restraining cables or some other means to prevent the patient's body from sliding due to the horizontal force vector. The present invention eliminates this need for a hospital bed frame.

Cable 18 pulls the harness approximately parallel to slanted surface 30 so that traction is properly applied pulling towards the patient's feet and slightly upward. At the same time, the upward angle of pull of cable 18 prevents the patient's thighs from being simply compressed against platform 12 without producing any traction on the spine.

Figure 5:
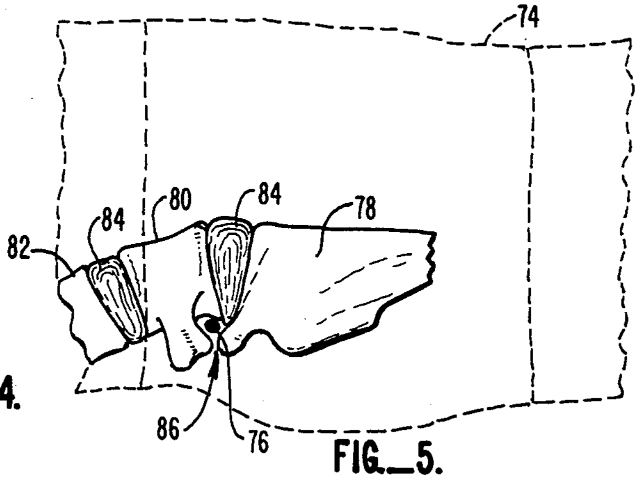
FIG. 5 is a side view of the lower spine of a patient in a supine position, with a portion of the patient's body shown in outline.
Figure 6:
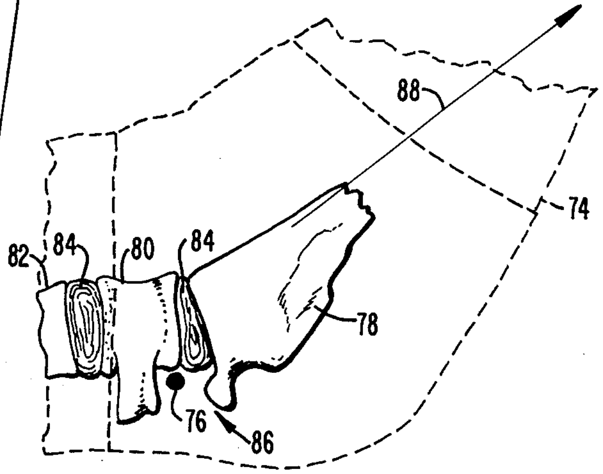
FIG. 6 is a side view of the lower spine of a patient with traction being applied by the embodiment of FIG. 1, with a portion of the patient's body shown in outline.

The beneficial effects of the present invention can be seen by reference to FIGS. 5 and 6. FIG. 5 shows the pelvis area of a patient standing in the erect position. The patient's body 74 is shown in phantom. A nerve root 76 is shown being pinched between sacrum 78 and a lumbar vertebral body 80. Vertebral body 80 is connected to adjoining sacrum 78 by an intervertebral disc 84. An apophyseal joint 86 is located between sacrum 78 and vertebral body 80.

FIG. 6 shows the pelvis area of a patient positioned on the present invention as described. By lifting the patient's thighs, the curve of the lumbar spine is reversed or flattened, which opens up apophyseal joint 86 thereby relieving the pressure on pinched nerve root 76. The addition of traction in the direction indicated by an arrow 88 distracts intervertebral discs 84 and further distracts apophyseal joint 86 while also acting to keep adjacent apophyseal joints and ligaments (not shown) at rest.

Figure 7:
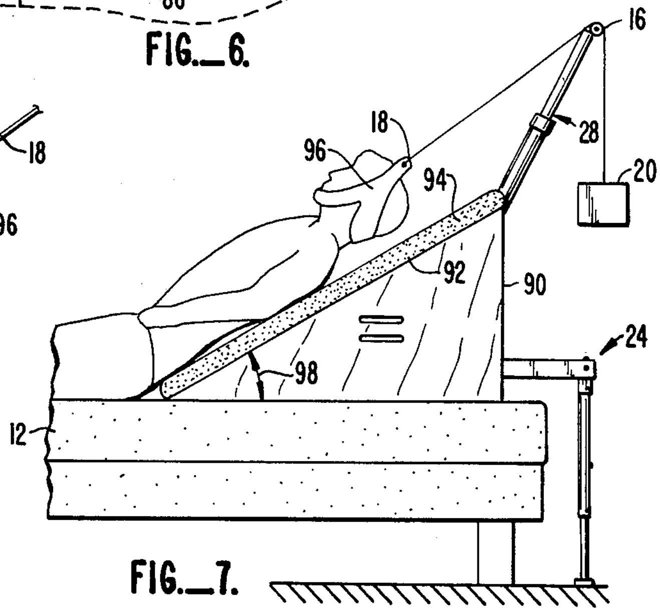
FIG. 7 is a side elevational view of the second preferred embodiment of the invention for applying cervical spine traction.

A second embodiment of the invention for use in cervical spine traction is shown in FIG. 7. The various elements of this embodiment are the same as that shown in FIG. 1, except that the shape of the platform used is different. A platform 90, instead of being trapezoidal like platform 12 as shown in FIG. 1, is triangular in shape with a single flat sloping surface 92 covered by a foam layer 94 against which a patient's back can rest. Cable 18 attaches to a head harness 96 attached to the head of a patient. Flat surface 92 is at an angle 98 to bed 39. The preferred magnitude of angle 98 is approximately 20°.

Weight 20 is attached to the end of cable 18, which passes over pulley 16, attached to telescoping arm 14, as in the embodiment shown in FIG. 1. Legs 24 are also present to add stabilization.

In operation, the second embodiment works in the same manner as already discussed for the first embodiment, except that traction is applied, using a chin harness or the like, to the patient's neck.

Figure 8:
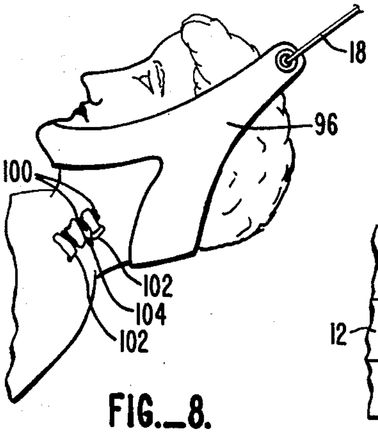
FIG. 8 is a side view of the cervical spine of a patient with traction being applied by the embodiment of FIG. 7.

The beneficial effects are similar to those for pelvic traction, as discussed earlier. FIG. 8 shows the effect of traction applied by the present invention on the cervical spine. As can be seen, by applying traction slightly upward through cable 18 attached to harness 96, cervical spine discs 100 are distracted, as well as joints 102, thus relieving pressure on a pinched nerve root 104.

As will be understood by those familiar with the art, the present invention may be embodied in other specific forms without departing from the spirit or essential characteristics thereof. For example, the cable may be looped over a suitable guideway or the like rather than a pulley. Accordingly, disclosure of the preferred embodiments of the present invention is intended to be illustrative, but not limiting, of the scope of the invention which is set forth in the following claims.

What is claimed is:

1. A self-contained traction device for use on a bed comprising:

a platform having a flat bottom surface and an upper surface which includes a portion inclined relative to said flat bottom surface, said inclined portion at its lowest point joining said bottom surface, said inclined portion having a width sufficient to support a portion of a person's body to be placed in traction, said platform having a length less than the length of said bed;

a pulley mounted to said platform proximate an upper end of said inclined portion; and flexible cable means looped over the pulley having a first end proximate the inclined portion and attached to the person's body and a second end connected to a weight.

2. The traction device of claim 1 further comprising cushion means on the upper surface of said platform for cushioning the portion of a person's body disposed on said platform.

3. The traction device of claim 1 further comprising at least one support leg having a first end attached to the platform and a second end adapted to be placed on a floor upon which said bed is resting for stabilizing the platform.

4. The traction device of claim 3 wherein the support leg includes means for adjusting its length.

5. The traction device of claim 4 wherein the support leg has an L-shape, and wherein the adjusting means includes means for adjusting the length of the leg in a substantially perpendicular direction to said floor.

6. The traction device of claim 5 wherein the support leg has first and second members and means connecting the members to each other and permitting movement of the members between aligned and substantially perpendicular positions with respect to each other, and wherein the platform includes track means disposed inside the platform connecting the support leg to the platform and receiving the members within the platform for storage.

7. The traction device of claim 1 further comprising an adjustable elongated member having a first end attached to the platform proximate said upper end of said inclined portion, the pulley being attached to a second free end of the elongated member.

8. The traction device of claim 7 including means for retracting the elongated member within the platform for storage.

9. The traction device of claim 1 further comprising handle means attached to the platform for aiding the manual handling and transportation of the platform.

10. The traction device of claim 1 wherein the inclined portion is flat and extends from the flat bottom surface at one end of the platform angularly upward to the other end of the platform and is adapted to support the back of a person sitting on said bed.

11. The traction device of claim 1 wherein said upper surface comprises said inclined portion extending angularly upward and adapted to support the thighs of a person lying on said bed and a second flat horizontal section extending from the inclined portion and adapted to support said person's calves.

12. The traction device of claim 1 wherein the pulley comprises a rotatably mounted pulley.

13. A self-contained traction device for use on a bed comprising:

a platform having a flat bottom surface and an upper surface inclined relative to said bottom surface, said inclined surface joining said bottom surface at its lowest point and extending from the flat bottom surface in an upward direction across the entire length of the platform, the upper surface having a width sufficient to support the back of a person to be placed in traction an extensible elongated member mounted to the platform proximate an upper end of the upper surface;

a pulley attached to the end of the elongated member;

leg stand means mounted to the platform proximate the elongated member for providing additional stability to the platform; and flexible cable means looped over the pulley having a first end proximate the upper portion and attached to the person's body and a second end connected to a weight.

14. A self-contained traction device for use on a bed comprising:

a platform having a flat bottom surface, a first upper surface inclined relative to said bottom surface, said first upper surface joining said bottom surface at its lowest point, and a second upper surface joining said first upper surface at its highest point, said second upper surface being substantially parallel to said bottom surface, said first and second upper surfaces having a width sufficient to support the legs of a person to be placed in traction;

an extensible elongated member mounted to the platform proximate an end of said second upper surface opposite said first upper surface;

a pulley attached to the end of the elongated member;

leg stand means mounted to the platform proximate the elongated member for providing additional stability to the platform; and flexible cable means looped over the pulley having a first end proximate the first upper surface and attached to the person's body and a second end connected to a weight.

* * * * *